United States Patent [19]

McDonald et al.

[11] Patent Number: 5,554,130
[45] Date of Patent: Sep. 10, 1996

[54] STICK-FREE SYRINGE AND ASSOCIATED METHODS

[75] Inventors: James McDonald, Monson; Charles N. Sturtevant, III, Braintree, both of Mass.; John Monteith, Hollidaysburg, Pa.; Mark Monteith, Lake Mary, Fla.

[73] Assignee: Creative Bio Tech, Inc., Hollidaysburg, Pa.

[21] Appl. No.: 443,597

[22] Filed: May 17, 1995

[51] Int. Cl.⁶ ..................................... A61M 5/32
[52] U.S. Cl. ................ 604/198; 604/263; 128/763
[58] Field of Search ..................... 604/110, 187, 604/192, 195, 198, 263; 128/763–765

[56] References Cited

U.S. PATENT DOCUMENTS

| | | |
|---|---|---|
| 4,392,859 | 7/1983 | Dent . |
| 4,813,940 | 3/1989 | Parry . |
| 4,892,107 | 1/1990 | Haber . |
| 4,964,866 | 10/1990 | Szwarc . |
| 5,015,234 | 5/1991 | Jullien . |
| 5,019,044 | 5/1991 | Tszo . |
| 5,030,209 | 7/1991 | Wanderer et al. ............ 604/198 |
| 5,086,780 | 2/1992 | Schmitt .................... 128/763 |
| 5,102,397 | 4/1992 | Brunet . |
| 5,137,521 | 8/1992 | Wilkens ................... 604/198 |
| 5,161,681 | 10/1992 | Kemp et al. . |
| 5,188,597 | 2/1993 | Sweeney et al. . |
| 5,242,416 | 9/1993 | Hutson . |
| 5,267,972 | 12/1993 | Anderson . |
| 5,269,761 | 12/1993 | Stehrenberger . |
| 5,273,543 | 12/1993 | Bell et al. . |
| 5,295,966 | 3/1994 | Stern et al. . |
| 5,300,040 | 4/1994 | Martin . |
| 5,308,329 | 5/1994 | Mazur et al. . |
| 5,328,473 | 7/1994 | Fayngold et al. ............ 604/263 X |

*Primary Examiner*—John D. Yasko
*Attorney, Agent, or Firm*—Lappin & Kusmer

[57] ABSTRACT

A stick-free blood collection system includes elongated inner and outer sheaths and a syringe, including a needle and blood collection tube, mounted with the inner sheath. The inner sheath—and hence the syringe—are axially moveable within the outer sheath. The outer sheath has a small aperture at the distal end thereof to permit passage of the needle through the outer sheath and into the patient. The outer sheath also includes an angled flat portion at the distal end to mount the outer sheath onto the patient in a practical fashion whereby the needle can be telescopically injected into the patient. During operation, the outer sheath is mounted at an angle relative to the surface of the patient, and the needle enters the surface at that angle to draw blood therein. The inner and outer sheaths have mating interconnections which engage when a user twists the inner sheath relative to the outer sheath, thereby preventing axial displacement of one sheath relative to the other sheath. Via this twisting motion, a user of the invention secures the needle within the outer sheath so as to prevent inadvertent contact with the used needle. The interconnections also generate an audible "click" when becoming engaged, thereby indicating that the system is safely locked. An aiming slot provides for visual access of the needle along the elongated axis; and the slot and the interface section provide a target site to predict the entry point of the needle into the patient. A lip at the distal end of the inner sheath provides for convenient handling of the inner sheath and syringe, and provides for smooth control of the system during replacement of the blood collection tube, e.g., a vacu-chamber.

22 Claims, 4 Drawing Sheets

# STICK-FREE SYRINGE AND ASSOCIATED METHODS

BACKGROUND

Medical syringes are used widely by the medical community to extract blood from patients. However, the handling and disposal of such syringes has always been problematic. In particular, the handling of used needles is of prime importance because of the safety risks faced by health care providers. For example, AIDS and other diseases can be transmitted by inadvertent contact with a used needles; and, therefore, such contact should be avoided to the full extent possible.

The methods in the prior art have attempted to deal with these problems. For example, one prior art syringe, U.S. Pat. No. 5,102,397, utilizes a pliable sleeve to orient the needle when not in use. Other prior art methods include (i) a "single use" blood collection device, U.S. Pat. No. 4,892,107, and (ii) a needle guard which destroys the needle after use, U.S. Pat. No. 5,015,234. Still other prior art syringes utilize various forms of needle guards, or complex locking mechanisms, such as shown and described in U.S. Pat. Nos. 5,242,416, 5,267,972, and 5,269,761.

Each of the aforementioned prior art syringe systems have certain drawbacks for effectively handling used syringe needles. Further, such systems often lack practical compatibility with the health care worker. That is, syringe systems which are designed to protect the health care worker from the used needles are typically bulky and/or difficult to wield in a clinical setting.

It is, accordingly, an object of the invention to provide a stick-free syringe which reduces the afore-mentioned difficulties.

Still another object of the invention is to provide a syringe which is physiologically compatible with normal use of the syringe, and which securely and safely stores the needle after use.

SUMMARY OF THE INVENTION

The invention provides, in one aspect, a sheath for controlling a hypodermic syringe of the type which includes (i) a blood collection tube and (ii) a hypodermic needle for drawing blood from a patient and into the tube. The sheath has an elongated tubular safety holder which forms an axial cavity between a distal end and a proximal end. The distal end includes an aperture with a diameter that is greater than the diameter of the needle and less than the diameter of the tube. The holder is structured to slideably engage the syringe within the cavity and between a first position, where the needle protrudes through the aperture, and a second position, where the holder substantially encloses the needle. Finally, the sheath includes and engagement section for securing the syringe at the second position such that the syringe is substantially restricted from movement along the elongated axis of the holder. A user of the sheath typically has control over the movement of the syringe between the first and second positions by control of the engagement section.

In another aspect, the sheath of the invention includes a patient interface, rigidly connected with the sheath, for mounting the distal end onto the patient. The patient interface is non-interfering with the axial movement of the syringe and has a substantially flat portion for stabilizing contact between the sheath and the patient. The flat portion forms a relatively rigid angle relative to the axial cavity of the sheath, thereby controlling the angle at which the needle enters the patient. Preferably, the angle of the flat portion, relative to the axial cavity, and hence relative to the needle, is between approximately 10 and 80 degrees. Most preferably, this angle is about 45 degrees.

The sheath of the invention includes a gripping section, according to another aspect of the invention. The gripping section provides control of the syringe within the sheath. Specifically, the gripping section provides practical control of the syringe within, and along the elongated axis of, the sheath. With the gripping section, the sheath of the invention, and hence the syringe therein, are conveniently controlled by a user of the sheath.

In still another aspect, the holder includes a substantially flat portion at the distal end for mounting the holder onto the patient. The flat portion stabilizes the contact between the sheath and the patient, and forms an angle relative to the elongated axis of the sheath, thereby controlling the angle at which the needle enters the patient's body and draws blood from within.

Preferably, the sheath of the invention is formed of a transparent, medically-accepted material so that a user can visually monitor the blood flow into the tube and within the sheath. Suitable materials include those materials in the polyethylene, polypropylene and polycarbonite families.

In yet another aspect, the engagement section includes a latch for securing the syringe at the second position selectively. The latch is connected to the holder and is moveable between a first engaged position, wherein the latch engages the syringe to prevent movement of the syringe along the elongated axis, and a non-engaged position, wherein the latch permits movement of the syringe along the elongated axis.

The holder can provide, in another aspect of the invention, a lip extending outwardly and substantially circumferentially about the holder at the distal end thereof. The lip thus provides a human grip to grasp and control the sheath in an effective manner. It further permits the smooth exchange of blood collection tubes in and out of the sheath.

In a preferred aspect of the invention, the engagement section includes a locking subsystem for selectively restricting axial movement of the syringe within the holder upon a rotational twist, about the elongated axis, of the holder relative to the syringe. Accordingly, a user of the invention can "lock" the needle within the holder, in the second position, upon twisting the syringe within the holder. The rotational twist required to achieve the "lock" position is between approximately 20 and 180 degrees. However, a preferred rotational twist is approximately 90 degrees, i.e., a one-quarter twist. In addition, the twist is preferably in a clockwise direction, when viewing the proximal end of the sheath.

In another aspect, a noticeable sound is generated by the sheath when engaging the lock position. Specifically, the locking subsystem includes a sound actuator which generates a audible "click" when the lock position is achieved. Accordingly, a user of the invention can readily ascertain that the used needle is secured safely within the sheath by listening for the audible click.

The invention also provides a blood collection system for controlling and securing a hypodermic needle. The blood collection system includes a tubular safety holder that forms an axial cavity between a distal end and a proximal end. The blood collection system also has a syringe of the type which includes (i) a blood collection tube and (ii) a hypodermic needle for drawing blood from a patient and into the tube, the syringe being telescopically disposed within the axial cavity of the holder. The blood collection system further has an engagement section for slideably engaging the syringe within the cavity and between a first position, wherein the needle protrudes from the distal end, and a second position, wherein the holder substantially encloses the needle.

The blood collection system also includes (i) a latching section for securing the syringe at the second position such that the syringe is substantially restricted from movement along the elongated axis, and (ii) a patient interface section, rigidly connected with the holder, for mounting the distal end onto the patient. The patient interface section has a substantially flat portion which stabilizes the contact between the sheath and the patient. The flat portion is formed at in angle relative to the elongated axis of the sheath, thereby controlling the angle at which the needle enters the patient when the flat portion is flush against the patient.

In still another aspect, the needle of the blood collection system has a first diameter, and wherein the distal end forms an aperture with a second diameter that is greater than the first diameter such that the needle passes unrestricted through the aperture.

In accord with another aspect, the latching section also prevents rotational movement of the syringe relative to the holder. That is, when engaged, the latching section prevents both axial and rotational movements of the syringe relative to the holder.

According to another aspect of the invention, an aiming slot is provided through the holder such that a user of the system can visually site the needle during use. More particularly, the aiming slot is an axial slot along the top of the system and near the distal end of the holder. When the syringe, and hence the needle, travel from the second position to the first position, at least part of the needle is visible to the user so that she has knowledge of when the needle will prick the patient. Further, the aiming slot and the patient interface section collectively form a target site, i.e., a location predicting the entry location of the needle in the patient. The target site provides for convenient and accurate aiming of the needle into the patient, analogous to the cross-hairs of a rifle scope: the needle within the aiming slot provides one axis of the site; and the patient interface section has an edge which, except for the aperture, forms the other axis, as the edge crosses the axis of the needle at the insertion point.

The invention thus provides several advantages. It ensures the safety of the heath care provider because the syringe is operated in conjunction with the sheath, and the needle is withdrawn and locked within the sheath immediately after drawing blood from the patient. Accordingly, the needle is stored securely within the sheath, thereby preventing inadvertent contact with the used needle. The terminal, or distal end of the sheath is closed except for the small aperture through which the needle is inserted into the patient. The same needle is withdrawn back through the aperture, which is much smaller than a human finger, again preventing inadvertent contact with the used needle.

Another advantage of the invention concerns the integrity of the normal blood collection procedure. Specifically, in certain aspects of the invention, the flat portion of the protective sheath is angled at about 45 degrees relative to the axis of the needle Accordingly, in operation, the flat portion can be placed comfortably flush on the patient's arm, or other insertion locations, and the needle can thereafter be telescopically injected directly into the appropriate part of the patient and along the axial cavity of the sheath.

The distal end of the sheath includes a lip that provides still other advantages. Specifically, the lip provides a finger placement location for the user to ensure the smooth exchange of blood collection tubes and proper and adequate stabilization of the syringe.

The latching section of the invention is preferably an efficient locking mechanism which is triggered by the withdrawal of the needle into the sheath while the sheath is in contact with the patient at the point of insertion. Once the needle is completely withdrawn to the second position, a twist of approximately ¼ turn secures the needle into a locked position (this twisting motion is preferably in a clockwise direction, when viewing the proximal end of the safety holder or sheath). Accordingly, the health care provider is never exposed to the needle as the needle is protected by the sheath during insertion and withdrawal, and the needle is locked in place before the sheath is removed from the surface of the patient. This locking action can be accomplished with only one hand.

The invention also provides, in another aspect, a system for controlling a hypodermic syringe of the type including a blood collection tube and a hypodermic needle. An elongated outer sheath forms an axial cavity between an outer distal end and an outer proximal end. The distal end of the outer sheath forms an aperture with a diameter that is greater than the diameter of the needle and less than the diameter of the tube. An elongated inner sheath is disposed telescopically within the outer sheath, and has an inner distal end and an inner proximal end. A threaded portion at the inner distal end provides for mounting the needle rigidly to the inner sheath such that the needle extends outwardly away from the inner distal end and along the axial cavity. According to this aspect, the inner sheath—and hence the needle—are moveable along the axial cavity and between a first position, wherein the needle protrudes through the aperture, and a second position, wherein the outer sheath substantially encloses the needle. The outer sheath further has a first mating interconnection; and the inner sheath further has a second mating interconnection. The first and second mating interconnections are interlocking at the second position upon the axial rotation of the inner sheath relative to the outer sheath, wherein the inner sheath is substantially immovable, relative to the outer sheath, along the axial cavity.

Preferably, the second position of the inner sheath also corresponds to a fully retracted position of the inner sheath relative to the outer sheath. Accordingly, in another aspect of the invention, the outer sheath has a third mating interconnection, and the inner sheath has a fourth mating interconnection which, collectively, form a "stop" at the second position. That is, a user of the system pulls the inner sheath backwards, i.e., away from the outer distal end of the outer sheath, until the third and fourth mating interconnections join to stop further backward and axial movement of the inner sheath relative to the outer sheath.

The patient interface section has an additional advantage in that it helps to stabilize the sheath when at rest on a table. For example, when the needle is safely stored within the sheath, after use, a user might normally place the sheath and syringe onto a table or tray. In accord with the invention, the patient interface section, and particularly the flat portion, helps keep the sheath from rolling around on the table or tray, thereby providing an additional safety feature.

The sheath of the invention is preferably a one-use system. That is, once the needle is withdrawn and secured within the sheath, the entire assembly is discarded. Accordingly, the locking action between the inner and outer sheaths at the second position can be permanent, in accord with this aspect of the invention. Further, another aspect of the invention includes an adhesive label which can be placed over the mating interconnections to prevent tampering and an attempted re-use of the system.

The invention is next described further in connection with preferred embodiments, and it will become apparent that various additions, subtractions, and modifications can be made by those skilled in the art without departing from the scope of the invention.

BRIEF DESCRIPTION OF THE DRAWINGS

A more complete understanding of the invention may be obtained by reference to the drawings, in which.

DETAILED DESCRIPTION OF THE DRAWINGS

Figure 1:
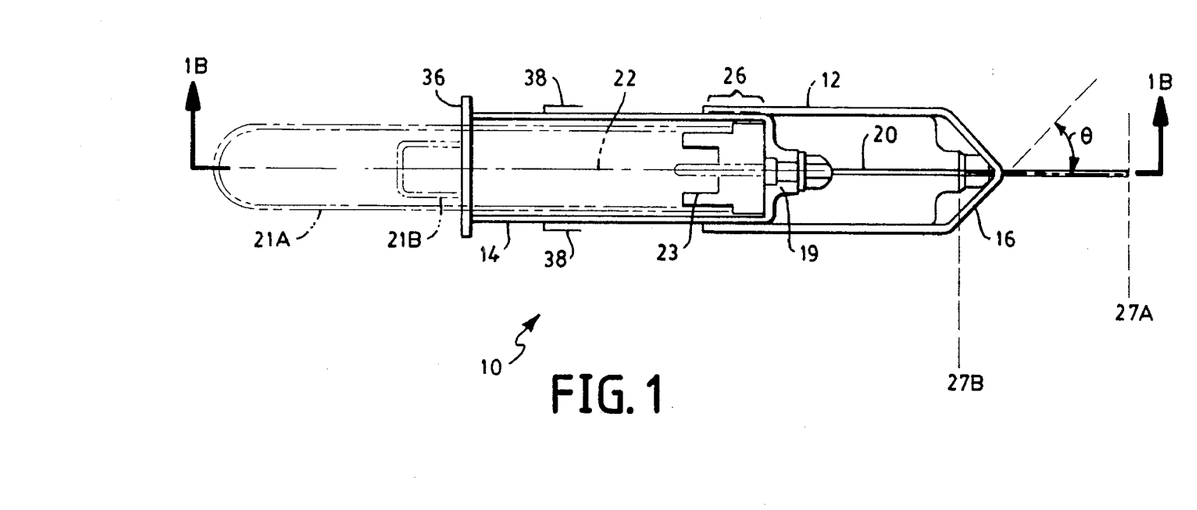
FIG. 1 illustrates a cross-sectional side view of a blood collection system constructed according to the invention.
Figure 1A:
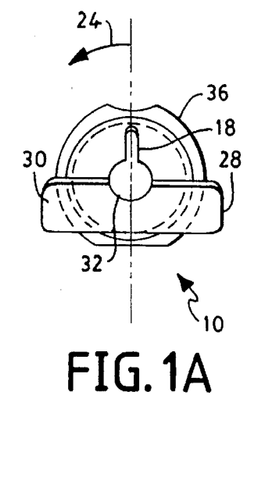
FIG. 1A shows a frontal view of the blood collection system of FIG. 1.
Figure 1B:
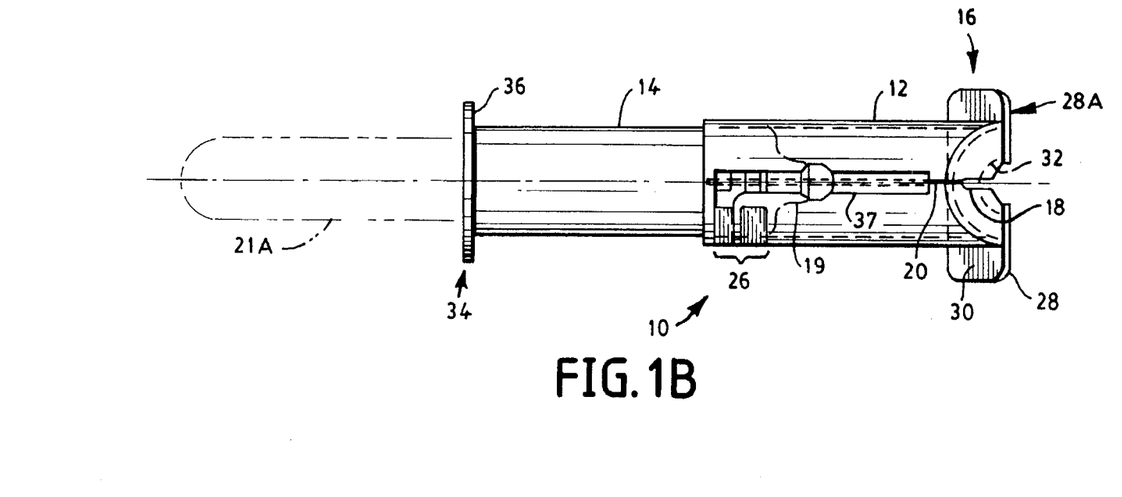
FIG. 1B illustrates a top plan view of the blood collection system of FIG. 1.

FIGS. 1–1B show three views of a blood collection system 10 constructed according to the invention. The system 10 has an outer elongated sheath 12 and an inner sheath 14 telescopically disposed within the sheath 12. The outer sheath 12 has a distal end 16 which is substantially sealed except for a small aperture 32, permitting the passage of the hypodermic needle 20 therethrough. The needle 20 is threaded directly into the inner sheath 14 at the threading section 19, described in more detail below; and a blood collection tube 21, e.g., a vacu-chamber (known to those skilled in the art, and illustratively shown in two standard sizes, A and B), is telescopically disposed within the inner sheath and onto the needle 20. The tube 21 has a pliant end section 23 which is punctured when mounted on the needle 20 (the tube 21 and needle 20 form, collectively, a hypodermic syringe such as known to those skilled in the art), and which is self-sealing when withdrawn from the sheath 14. In normal operation, blood is drawn through the needle 20 and into the tube 21.

The inner and outer sheaths 12, 14 can be twisted, relative to each other and about the elongated axis 22 (the motion 24 is illustratively shown as in FIG. 1A, wherein the motion 24 corresponds to the movement of the inner sheath relative to the outer sheath), to lock the two sheaths together such that they are substantially immovable, relative to each other, along the axial direction 22. This locking action is accomplished by mating interconnections 26 between the two sheaths, as described in more detail below. In addition, in the illustrated embodiments shown and described below, the mating interconnections 26 further render the two sheaths substantially immovable, relative to each other, in rotation about the elongated axis, e.g., in movements such as shown by motion 24, FIG. 1A.

FIGS. 1A and 1B also illustrate the aiming slot 18, which provides visual access to the needle 20 by a user of the invention prior to penetrating the patient. FIG. 1B also shows the guide slot 37, which stabilizes the axial movement of the inner sheath 14 relative to the outer sheath 12.

The purpose of the locking action between the inner and outer sheaths 12, 14 is illustrated in FIG. 1. Specifically, the combination of the needle 20, tube 21, and inner sheath 14 is axially moveable—along the guideslot 37 and within the outer sheath 12—between a first position 27A, where the needle 20 protrudes from aperture 32, and a second position 27B, where the needle 20 is enclosed within the sheath 12, except for the aperture 32. The twisting of the two sheaths 12, 14 relative to each other at the second position 27B facilitates the locking action between the sheaths 12, 14, and thus "locks" the needle 20 within the outer sheath 12. In one embodiment of the invention, a suitable travel distance between positions 27B and 27A is about 1.2 inches.

FIGS. 1A and 1B show the patient interface section 28, which is formed integrally with the outer sheath 12, and which includes a flat portion 30 (in an alternative embodiment (not shown), the interface section can be a separate component that is mounted rigidly with the outer sheath 12). The interface section 28 forms part of the scalloped aperture 32 so that it is non-interfering with the axial movement of the needle 20. The flat portion 30 is used to mount the distal end 16 against the patient so as to stabilize the system 10 while a user of the system 10 draws blood from a patient. As such, the flat portion 20 is angled relative to the axis 22 (this angle is illustratively shown as angle θ, representing the angle between the needle 20, along the elongated axis 22, and the surface of the flat portion 30). Preferably, the angle θ is about forty-five degrees. However, for certain applications, the system 10 can include a flat portion 30 that has an angle θ between about ten and eighty degrees.

The aiming slot 18 and the patient interface section 28 collectively form a target site, i.e., a location predicting the entry location of the needle 20 in the patient. The target site provides for convenient and accurate aiming of the needle into the patient. Specifically, the needle 20 within the aiming slot 18 provides one axis of the target site; and the edge 28A of the patient interface section forms the other axis. A user perceives that those two axes cross at the insertion point even though the aperture 32 is at the center of the site. This site is very useful in determining the insertion point, e.g., into a vein.

At the proximal end 34, the inner sheath 14 preferably has a lip 36 that may be grasped by the fingers of a user of the system 10. The lip 36 thus provides a grip from which a user can control the syringe 21, 20—i.e., the combination of the tube 21 and needle 20—within the sheath 12. By pulling or pushing on the lip 36 relative to the outer sheath 12, the inner sheath 14 and syringe 21, 20 are displaced axially relative to the outer sheath 12.

In operation, a user grasps the outer sheath 12 with the forefingers, and pushes the lip 36 with the thumb to move the needle 20 and inner sheath 14 from the second position 27B to the first position 27A. In such an action, and providing that the flat portion 30 is mounted at the desired location on the patient, the needle 20 punctures the patient so that blood can be withdrawn (typically, a plurality of vacu-chambers 21 are sequentially mounted onto the needle 20 within the sheath 14, and each vacu-chamber 21 sucks blood for storage therein). After blood is withdrawn, the user pulls the lip 36 while simultaneously securing the outer sheath 12 against the patient (i.e., such that the flat portion 30 remains in contact with the patient). Once the needle 20 and inner sheath 14 are again at position 27B, the user twists the inner sheath 14 relative to the outer sheath 12 to "lock" the needle 20 within the outer sheath 12. In the illustrated embodiment, this locking action is accompanied by an audible "click," which is generated by the mating interconnections 26 described in more detail below. In addition, once this locking action is completed, e.g., when the interconnections 26 generate the audible "click" sound, the inner and outer sheaths are immovable, relative to each other, along the axis 22, and in a rotational direction about the axis 22, such as illustrated by motion 24, FIG. 1A.

The inner sheath 14 has a sliding connecting element 38 which grasps the outer sheath 12 when the syringe 21, 20 is moved from the second position 27B to the first position 27A. This engagement between the inner and outer sheaths 14, 12 helps to stabilize the entire system 10 during blood collection activities. In one embodiment of the invention, a suitable distance between the lip 36 and the element 38 is about one-half inch, i.e., a size which is sufficient to accommodate a human finger.

Figure 2:
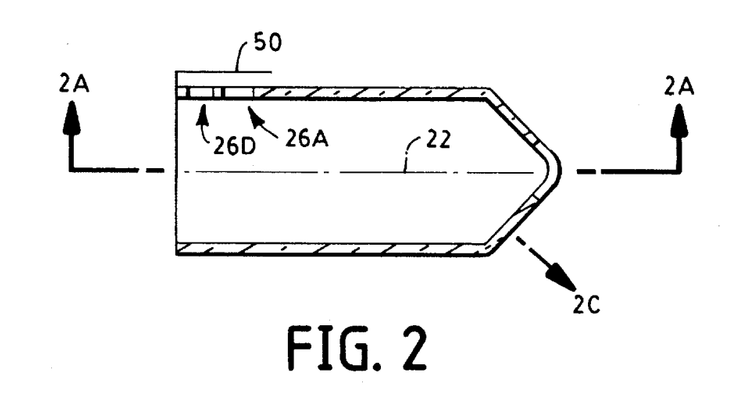
FIG. 2 illustrates a cross-sectional view of an outer sheath constructed according to the invention.
Figure 2A:
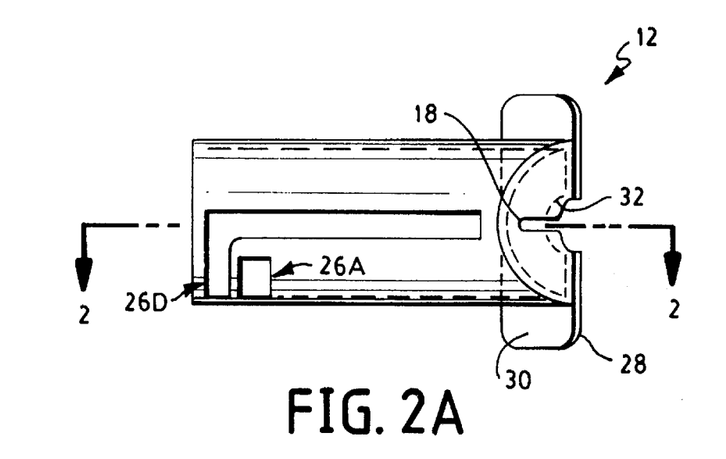
FIG. 2A shows a top plan view of the outer sheath of FIG. 2.
Figure 2B:
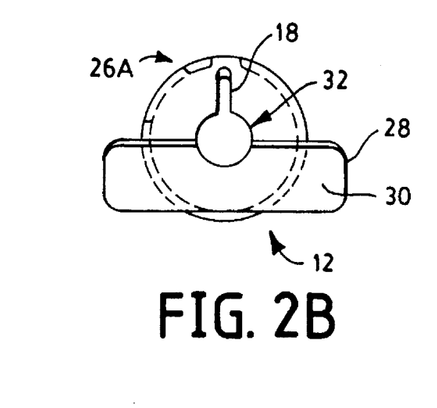
FIG. 2B shows a frontal view of the outer sheath of FIG. 2.
Figure 2C:
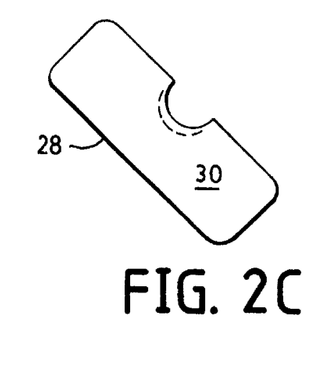
FIG. 2C illustrates a patient interface, constructed according to the invention, rigidly connected with the outer sheath of FIG. 2.

FIGS. 2–2B show further views and details of the outer sheath 12 of FIG. 1; and FIG. 2C shows further detail of the flat portion of the patient interface 28. In particular, FIG. 2 shows a cross-sectional view of the outer sheath 12, including the first mating interconnection 26A, which rotationally locks with the second mating interconnection 26B shown in FIGS. 3–3A. FIG. 2A shows a top plan view of the outer sheath 12, while FIG. 2B shows a front view of the sheath 12, including the patient interface 28 and flat portion 30 (shown also in FIG. 2C). The third mating interconnection 26D forms a stop with the fourth mating interconnection 26C of FIGS. 3–3A.

Figure 3:
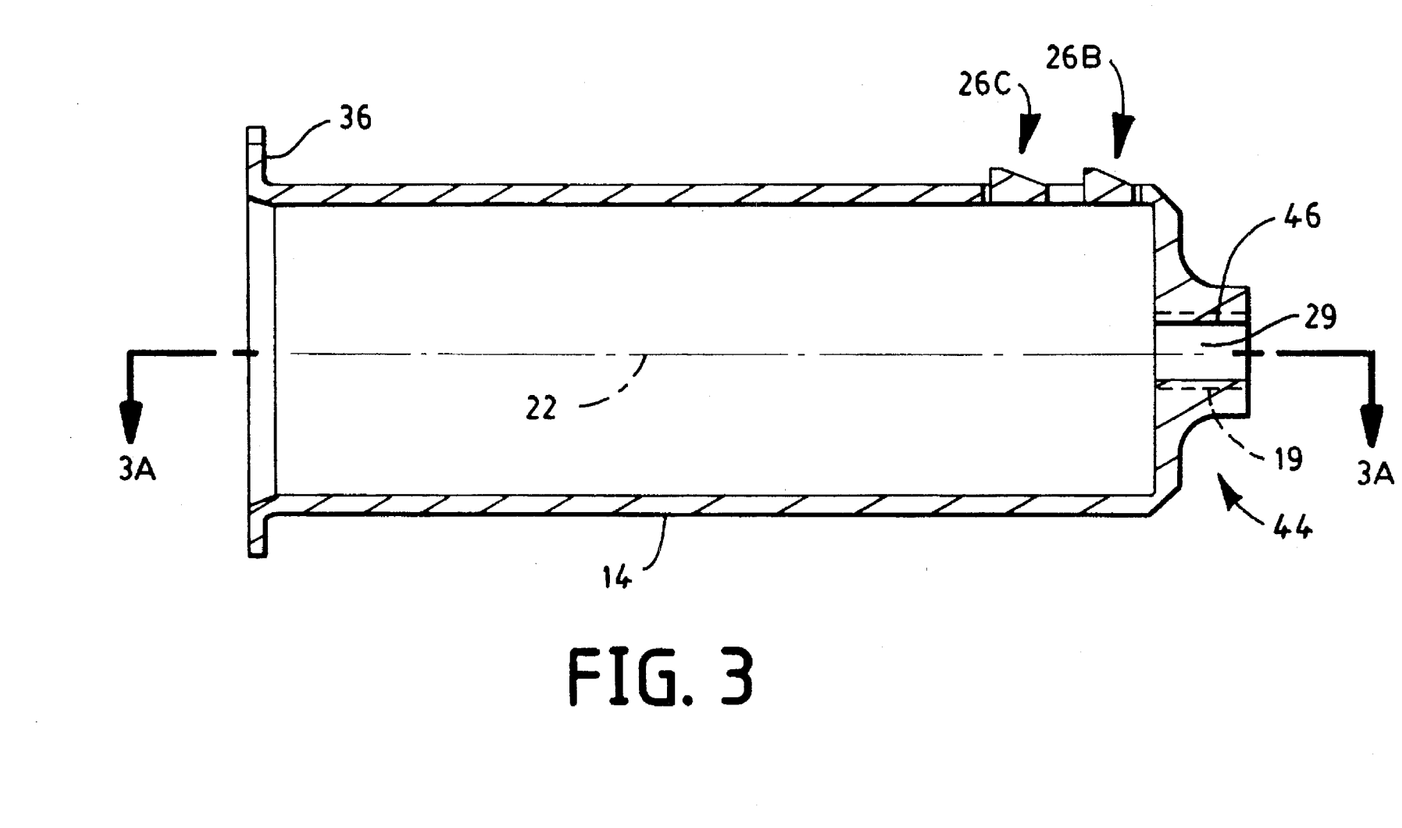
FIG. 3 illustrates a cross-sectional view of an inner sheath constructed according to the invention.
Figure 3A:
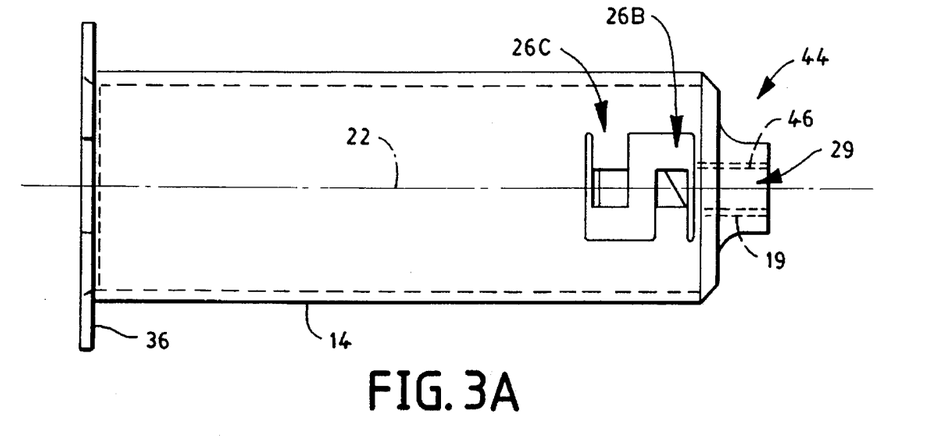
FIG. 3A shows a top plan view of the inner sheath of FIG. 3.
Figure 3B:
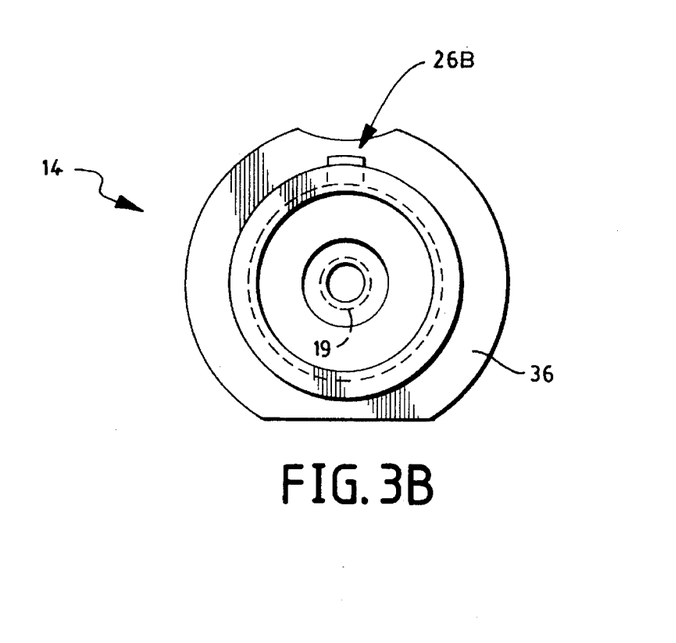
FIG. 3B shows a frontal view of the outer sheath of FIG. 3.

FIGS. 3–3B show further views and detail of the inner sheath 14 of FIG. 1. In particular, FIG. 3 shows a cross-sectional view of the inner sheath 14, including a second mating interconnection 26B, which rotationally locks with the mating interconnection 26A of FIGS. 2–2A, and a fourth mating interconnection 26C, which forms the stop with mating interconnection 26D of FIGS. 2–2A The end 44 of the inner sheath 14 forms the aperture 29 which has threading 19 along the inside wall 46 so as to mate with standard hypodermic needle threading (known to those skilled in the art).

More particularly, and with reference to FIGS. 2–2B, 3–3B, the interconnection 26B is a cam which is slanted (see FIG. 3), so that when the inner sheath 14 is twisted about the axis 22 (i.e., in a movement such as illustrated as motion 24 of FIG. 1A), the cam 26B slides underneath the outer sheath 12 and into the slot forming the interconnection 26A. When the cam 26B enters the slot 26A, an audible "click" is heard, thereby notifying the user of the invention that the needle is secured within the sheath. In the illustrated embodiment, once the cam 26B is within the slot 26A, the inner sheath 14 is rotationally (clockwise and counter-clockwise) and axially immovable relative to the outer sheath 12. An adhesive cover 50 (illustratively shown as a free-standing plastic strip 50 in FIG. 2) can be applied onto the interconnections 26 to prevent tampering of the sheath and to prevent the attempted re-use of the system.

Further, the interconnection 26C forms a substantially rigid stop with the interconnection 26D. A user can thus pull the inner sheath 14 backwards, i.e., away from the distal end of the outer sheath 12, until the interconnections 26C, 26D engage, which is as far as the inner sheath can travel in that direction.

It should be apparent to those skilled in the art that certain modifications can be made to the invention as described herein without departing from the scope of the invention. For example, the dimensions shown in FIGS. 1–3 are illustrative of one preferred embodiment only; and those skilled in the art can construct the invention with other dimensions and fall within the scope of the claims below.

In view of the foregoing, what is claimed as new and secured by the Letters Patent is:

1. A sheath for controlling a hypodermic syringe, the syringe of the type which includes (i) a blood collection tube and (ii) a hypodermic needle for drawing blood from a patient and into the tube, comprising:

an elongated tubular safety holder forming an axial cavity between a distal end and a proximal end, the distal end forming an aperture with a diameter that is greater than the diameter of the needle and less than the diameter of the tube, the holder having means for slideably engaging the syringe within the cavity and between a first position, wherein the needle protrudes through the aperture, and a second position, wherein the holder substantially encloses the needle, the holder further having a substantially flat portion at the distal end for mounting the holder onto the patient, the flat portion stabilizing contact between the sheath and the patient and forming an angle relative to the elongated axis of the sheath, thereby controlling the angle at which the needle draws blood from the patient, and means for securing the syringe at the second position such that the syringe is substantially restricted from movement along the elongated axis of the holder.

2. A sheath for controlling a hypodermic syringe, the syringe of the type which includes (i) a blood collection tube and (ii) a hypodermic needle for drawing blood from a patient and into the tube, comprising:

an elongated tubular safety holder forming an axial cavity between a distal end and a proximal end, the distal end forming an aperture with a diameter that is greater than the diameter of the needle and less than the diameter of the tube, the holder having means for slideably engaging the syringe within the cavity and between a first position, wherein the needle protrudes through the aperture, and a second position, wherein the holder substantially encloses the needle, means for securing the syringe at the second position such that the syringe is substantially restricted from movement along the elongated axis of the holder, and patient interface means, rigidly connected with the sheath, for mounting the distal end onto the patient, the patient interface means being non-interfering with axial movement of the syringe and having a substantially flat portion for stabilizing contact between the sheath and the patient, the flat portion forming an angle relative to the axial cavity of the sheath, thereby controlling the angle at which the needle enters the patient.

3. A sheath according to claim 2, wherein the angle is between approximately 10 and 80 degrees.

4. A sheath according to claim 1, further comprising gripping means for gripping and controlling the syringe within the sheath, the gripping means providing physiological control of the syringe within, and along the elongated axis of, the sheath.

5. A sheath according to claim 1, wherein the holder is formed of a transparent medically-accepted material.

6. A sheath according to claim 1, wherein the holder is formed of material selected from the group consisting essentially of polyethylene and polycarbonite.

7. A sheath according to claim 1, wherein the holder further comprises a lip extending outwardly and substantially circumferentially about the holder at the proximal end thereof, the lip providing a human grip to grasp and control the sheath.

8. A sheath for controlling a hypodermic syringe, the syringe of the type which includes (i) a blood collection tube and (ii) a hypodermic needle for drawing blood from a patient and into the tube, comprising:

an elongated tubular safety holder forming an axial cavity between a distal end and a proximal end, the distal end forming an aperture with a diameter that is greater than the diameter of the needle and less than the diameter of the tube, the holder having means for slideably engaging the syringe within the cavity and between a first position, wherein the needle protrudes through the aperture, and a second position, wherein the holder substantially encloses the needle, and means for securing the syringe at the second position such that the syringe is substantially restricted from movement along the elongated axis of the holder and for selectively restricting axial movement of the syringe within the holder upon a rotational twist, about the elongated axis, of the holder relative to the syringe.

9. A sheath according to claim 8, wherein the rotational twist is between approximately 20 and 180 degrees.

10. A sheath according to claim 8, wherein the means for securing the syringe at the second position further comprises means for restricting the rotational movement about the elongated axis of the syringe relative to the holder.

11. A sheath according to claim 8, wherein the means for securing the syringe at the second position further comprises means for generating an audible sound once the syringe is engaged at the second position.

12. A sheath according to claim 8, wherein the rotational twist is approximately 90 degrees and wherein the angle is approximately 45 degrees.

13. A sheath according to claim 1, further comprising an adhesive cover for selectively covering the means for securing the syringe at the second position, the adhesive cover protecting against a possible re-use of the sheath.

14. A blood collection system for controlling and securing a hypodermic needle, comprising:

an tubular safety holder forming an axial cavity between a distal end and a proximal end, a syringe including (i) blood collection tube and (ii) a hypodermic needle for drawing blood from a patient and into the tube, the syringe being telescopically disposed within the axial cavity, means for slideably engaging the syringe within the cavity and between a first position, wherein the needle protrudes from the distal end, and a second position, wherein the holder substantially encloses the needle, means for securing the syringe at the second position selectively such that the syringe is substantially restricted from movement along the elongated axis, and patient interface means, rigidly connected with the holder, for mounting the distal end onto the patient, the patient interface means having a substantially flat portion for stabilizing contact between the sheath and the patient, the flat portion forming an angle relative to the elongated axis of the sheath, thereby controlling the angle at which the needle enters the patient.

15. A blood collection system according to claim 14, wherein the needle has a first diameter, and wherein the distal end forms an aperture having a second diameter that is greater than the first diameter such that the needle passes unrestricted through the aperture.

16. A system for controlling a hypodermic syringe, the syringe of the type which includes (i) a blood collection tube and (ii) a hypodermic needle for drawing blood from a patient and into the tube, comprising:

an elongated outer sheath forming an axial cavity between an outer distal end and an outer proximal end, the outer distal end forming an aperture with a diameter that is greater than the diameter of the needle and less than the diameter of the tube, and an elongated inner sheath disposed telescopically within the outer sheath, the inner sheath having an inner distal end and an inner proximal end, and having first means at the inner distal end for mounting the needle rigidly to the inner sheath such that the needle extends outwardly away from the inner distal end and along the axial cavity, the inner sheath being moveable along the axial cavity and between a first position, wherein the needle protrudes through the aperture, and a second position, wherein the outer sheath substantially encloses the needle, wherein the outer sheath further comprises a first mating interconnection, and the inner sheath further comprises a second mating interconnection, the first and second mating interconnections being interlocking at the second position upon the axial rotation of the inner sheath relative to the outer sheath, wherein the inner sheath is substantially immovable, relative to the outer sheath, along the axial cavity.

17. A system according to claim 16, further comprising patient interface means for mounting the outer distal end onto the patient, the patient interface means being non-interfering with axial movement of the needle and having a substantially flat portion for stabilizing contact between the sheath and the patient, the flat portion forming an angle relative to the axial cavity of the sheath, thereby controlling the angle at which the needle enters the patient.

18. A system according to claim 16, wherein the inner sheath further comprises a lip extending outwardly and substantially circumferentially about the inner sheath at the inner proximal end thereof, the lip providing a human grip to grasp and control the sheath.

19. A system according to claim 16, wherein the first and second mating interconnections generating, in combination, an audible sound when the interconnections become locked.

20. A system according to claim 16, further comprising an aiming slot in the distal outer sheath, the aiming slot providing visual access to the needle during travel between the first and second positions.

21. A system according to claim 20, wherein the patient interface section and the aiming slot form, in combination, a target site for which a user of the system predicts entry of the needle into the patient.

22. A method for controlling a hypodermic syringe, the syringe of the type which includes (i) a blood collection tube and (ii) a hypodermic needle for drawing blood from a patient and into the tube, comprising the steps of:

mounting the needle to an elongated inner sheath that is telescopically disposed within an elongated outer sheath, the outer sheath forming (i) an axial cavity between an outer distal end and an outer proximal end, and (ii) an aperture with a diameter that is greater than the diameter of the needle and less than the diameter of the tube, the inner sheath having an inner distal end and an inner proximal end, the needle being mounted such that the needle extends outwardly away from the inner distal end and along the axial cavity, moving the inner sheath relative to the outer sheath and along the axial cavity between a first position, wherein the needle protrudes through the aperture, and a second position, wherein the outer sheath substantially encloses the needle, and locking the inner and outer sheaths together at the second position upon the axial rotation of the inner sheath relative to the outer sheath, wherein the inner sheath is substantially immovable, relative to the outer sheath, along the axial cavity.

* * * * *